United States Patent [19]

DeBernardis et al.

[11] Patent Number: 4,618,683
[45] Date of Patent: Oct. 21, 1986

[54] TETRAHYDRO-6,7-DIMETHOXY-1H-BENZ-[E]ISOINODOLINES USEFUL IN THE TREATMENT OF HYPERTENSION AND AS SEDATIVES

[75] Inventors: John F. DeBernardis, Lake Villa; Daniel J. Kerkman, Gurnee; William J. McClellan, Waukegan, all of Ill.

[73] Assignee: Abbott Laboratories, North Chicago, Ill.

[21] Appl. No.: 673,458

[22] Filed: Nov. 20, 1984

Related U.S. Application Data

[63] Continuation-in-part of Ser. No. 383,631, Jun. 1, 1982, abandoned.

[51] Int. Cl.[4] .................... C07D 491/02; A61K 31/40
[52] U.S. Cl. .................................. 548/420; 548/427
[58] Field of Search ............... 548/420, 427; 514/410, 514/411

[56] References Cited

U.S. PATENT DOCUMENTS 3,166,570  1/1965  Wintrop ............................ 548/427
3,890,347  6/1975  Middlemiss ........................ 548/427
4,259,471  3/1981  Keller et al. ..................... 260/465 H

FOREIGN PATENT DOCUMENTS 16862  4/1974  Japan ................................ 548/427

OTHER PUBLICATIONS

Lahiri et al, J. Med. Chem. 8, 131 (1965).
A. U. De et al, Chem. Abst., 61-16033g.
Lahiri et al, Journal of Pharmaceutical Sciences, vol. 57, 1968, 1013–1016.
Water et al, J. Med. Chem., vol. 18(2), 1975, pp. 206–208.
Langlois et al, Chem. Abst., 78-71826y (1973).
Burger, Medicinal Chem., p. 71 (3rd edition, part I).

*Primary Examiner*—Donald G. Daus
*Assistant Examiner*—Cecilia Shen
*Attorney, Agent, or Firm*—Steven F. Weinstock; Martin L. Katz

[57] ABSTRACT

Disclosed herein are tetrahydro-benzo[e]isoindolines represented by the formula

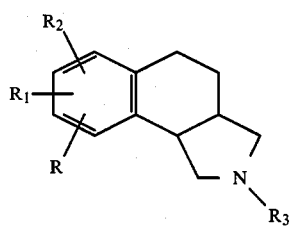

wherein R, $R_1$ and $R_2$ are independently selected from hydrogen, loweralkyl of 1 to 4 carbon atoms, hydroxy, loweralkoxy of 1 to 3 carbon atoms, allyloxy, benzyloxy, benzoyloxy, thiomethyl, halo,

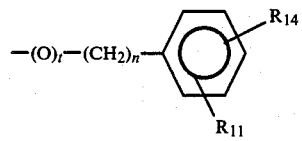

wherein t is 0 or 1, n is 0 to 5 and $R_{11}$ and $R_{14}$ are independently selected from hydrogen, halo, hydroxy, loweralkyl of 1 to 4 carbon atoms, loweralkoxy of 1 to 3 carbon atoms or amino; or R and $R_1$, or $R_1$ and $R_2$ can be taken together to form a methylenedioxy or ethylenedioxy bridge; with the proviso that at least one of R, $R_1$ or $R_2$ must be other than hydrogen and the proviso that two of R, $R_1$, or $R_2$ must be other than methoxy in the 7 and 8 positions when the remaining one of R, $R_1$ or $R_2$ is hydrogen; and $R_3$ is hydrogen, loweralkyl of 1 to 4 carbon atoms, halo-substituted loweralkyl of 1 to 4 carbon atoms, amino-substituted loweralkyl of 1 to 4 carbon atoms, amino-substituted arylalkyl, allyl, thioloweralkyl, loweralkanol, or

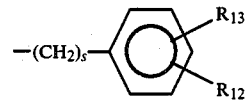

wherein $R_{12}$ and $R_{13}$ are independently selected from hydrogen, hydroxy, amino, loweralkoxy of 1 to 3 carbon atoms and s is 1 to 3; or

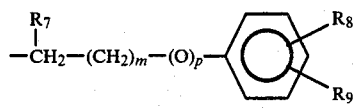

wherein m is 0, 1 or 2, p is 0 or 1, $R_7$ is hydrogen or loweralkyl of 1 to 4 carbon atoms and $R_8$ and $R_9$ are independently selected from hydrogen, hydroxy, methoxy, loweralkyl of 1 to 4 carbon atoms, or halo, or $R_8$ and $R_9$ can be taken together to form a methylenedioxy or ethylenedioxy bridge; or 1,4-benzodioxan of the formula

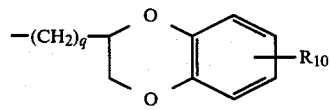

wherein q is 1, 2 or 3, and $R_{10}$ is hydrogen, methoxy, amino, or halo; and the pharmaceutically acceptable salts thereof.

17 Claims, No Drawings

TETRAHYDRO-6,7-DIMETHOXY-1H-BENZ-[E]ISOINODOLINES USEFUL IN THE TREATMENT OF HYPERTENSION AND AS SEDATIVES

BACKGROUND AND SUMMARY OF THE INVENTION

This application is a continuation-in-part of U.S. patent application, Ser. No. 383,631, filed June 1, 1982, now abandoned.

This invention relates to novel tetrahydrobenzo [e] isoindolines compounds.

The adrenergic nervous system plays a major role in the innervation of heart, blood vessel and smooth muscle tissue. Agents capable of interacting with receptor sites within the adrenergic nervous system can result in a variety of physiological responses, including but not limited to vasoconstriction, vasodilation, and increased or decreased heart rate (chronotropic), contractility (inotropic) and metabolic activity. In the past, various adrenergic agents have been employed to affect these and other physiological responses. However, it is highly desirable to obtain new adrenergic agents which demonstrate a high degree of specificity for differing receptor types within the adrenergic nervous system in order to obtain a desired physiological response separate from other possible, and perhaps less desirable, responses of the system. This property has been lacking from most previously employed adrenergic agents. Thus, the search continues for new and improved adrenergic agents capable of selective interaction with adrenergic receptor sites.

It has now been determined that a new class of compounds, the tetrahydro-benzo[e]isoindolines, as herein defined, demonstrate an ability to interact specifically with various adrenergic receptor types and are useful as therapeutic agents in the treatment of hypertension and as sedatives.

DESCRIPTION OF ILLUSTRATIVE EMBODIMENTS

The present invention provides tetrahydrobenzo[e]isoindolines represented by the formula I:

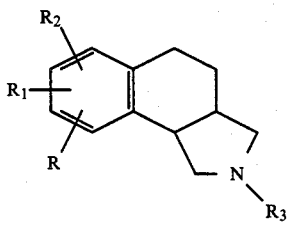

wherein R, $R_1$ and $R_2$ are independently selected from hydrogen, loweralkyl of 1 to 4 carbon atoms, hydroxy, loweralkoxy of 1 to 3 carbon atoms, allyloxy, benzyloxy, benzoyloxy, thiomethyl, halo,

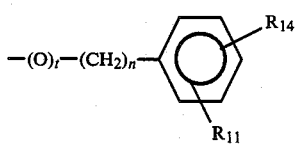

wherein t is 0 or 1, n is 0 to 5, and $R_{11}$ and $R_{14}$ are independently selected from hydrogen, halo, hydroxy, loweralkyl of 1 to 4 carbon atoms, loweralkoxy of 1 to 3 carbon atoms or amino; or R and $R_1$, or $R_1$ and $R_2$ can be taken together to form a methylenedioxy or ethylenedioxy bridge; with the proviso that at least one of R, $R_1$ or $R_2$ must be other than hydrogen and the proviso that two of R, $R_1$, or $R_2$ must be other than methoxy in the 7 and 8 positions when the remaining one of R, $R_1$ or $R_2$ is hydrogen; and $R_3$ is hydrogen, loweralkyl of 1 to 4 carbon atoms, halo-substituted loweralkyl of 1 to 4 carbon atoms, amino-substituted loweralkyl of 1 to 4 carbon atoms, amino-substituted arylalkyl, allyl, thioloweralkyl, loweralkanol, or

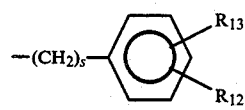

wherein $R_{12}$ and $R_{13}$ are independently selected from hydrogen, hydroxy, amino, loweralkoxy of 1 to 3 carbon atoms and s is 1 to 3; or

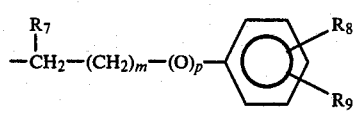

wherein m is 0, 1 or 2, p is 0 or 1, $R_7$ is hydrogen or loweralkyl of 1 to 4 carbon atoms and $R_8$ and $R_9$ are independently selected from hydrogen, hydroxy, methoxy, loweralkyl of 1 to 4 carbon atoms, or halo, or $R_8$ and $R_9$ can be taken together to form a methylenedioxy or ethylenedioxy bridge; or 1,4-benzodioxan of the formula

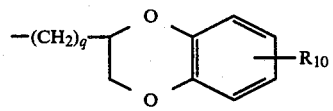

wherein q is 1, 2 or 3, and $R_{10}$ is hydrogen, methoxy, amino, or halo; and the pharmaceutically acceptable salts thereof.

Both cis and trans geometric isomers and enantiomeric isomers of the compounds of the invention are contemplated.

As used herein, the term "loweralkyl of 1 to 4 carbon atoms" means straight or branched chain saturated hydrocarbon radicals, such as methyl, ethyl, n-propyl, iso-propyl, n-butyl, s-butyl, and t-butyl. Additionally, the term "halo-substituted loweralkyl of 1 to 4 carbon atoms" means a loweralkyl group as defined above substituted by a halogen, such as, for example, trifluoromethyl, 2-trichloroethyl, and the like.

As used herein, the term "halo" means chloro, bromo, fluoro and iodo.

As used herein, the term "loweracyl" means an acyl group represented by the formula

wherein $R_{15}$ is loweralkyl as herein defined. Illustrative acyl groups useful in the practice of the invention are acetyl, n-propionyl, n-butyryl, s-butyryl, iso-butyryl, and the like.

As used herein, the term "loweralkoxy of 1 to 3 carbon atoms" means methoxy, ethoxy, and straight or branched propoxy.

As used herein, the term "amino" means a group represented by the formula, $NR_{16}R_{17}$, wherein $R_{16}$ and $R_{17}$ are independently selected from hydrogen and loweralkyl as herein defined.

As used herein, the term "arylalkyl" means a group having a loweralkyl chain as herein defined ending in an aromatic ring.

As used herein, the term "thioloweralkyl" means a compound of the formula $(CH_2)_bSH$ wherein b is 2 to 4 carbon atoms.

As used herein, the term "loweralkanol" means a straight chained or branched compound of the formula $(CH_2)_dOH$ wherein d is 2 to 4 carbon atoms.

The term "pharmaceutically acceptable salts" refers to the pharmaceutically acceptable, relatively nontoxic, inorganic or organic acid addition salts of the compounds of this invention. These salts can be prepared in situ during the final isolation and purification of the compounds, or by separately reacting the free base with a suitable organic or inorganic acid. Representative salts include the hydrochloride, hydrobromide, sulfate, phosphate, nitrate, bisulfate, acetate, oxalate, valerate, oleate, palmitate, stearate, laurate, borate, benzoate, lactate, phosphate, tosylate, citrate, maleate, fumarate, succinate, tartrate, napsylate and the like. It will be apparent to those skilled in the art that, depending upon the number of available amino groups for salt formation, the salt of this invention can be per-N-salts.

The foregoing may be better understood in connection with the following examples:

EXAMPLE 1

1-Cyano-5,6-dimethoxy-3,4-dihydronaphthalene

A solution of 5,6-dimethoxy-1-tetralone (30 g, 0.14 mole), trimethylsilylcyanide (15.8 g, 0.156 mole), ca. 15 mLs dry benzene, and catalytic $AlCl_3$ was stirred under $N_2$ at 70° (oil bath) for 15 hours. Benzene was removed (in-vacuo), 300 mL MeOH was added to the crude product, and the solution was stirred at 0°–10° C. as HCl was bubbled through the solution for 3 hours. Methanol was evaporated (in-vacuo) and ca. 500 mL water was added to the residue. The resultant solid was filtered, washed with water, and dried (under high-vacuum) to yield 29.2 g of yellow solid. (99.8%); $M^+215$; mp 139°–40° C.

EXAMPLE 2

1,2-Dicyano-5,6-dimethoxytetralin

A suspension of the compound of example 1 (29.2 g, 0.14 mole), 315 mL MeOH, and 110 mL diethyl ether was stirred mechanically, just below reflux temperature as a 45° solution of KCN (34 g, 0.52 mole) in 94 mL water was added dropwise, quickly. The reaction mixture was stirred at reflux for 1.5 hr. After cooling briefly a solution of $NH_4OAc$ (21 g, 0.27 mole) in 34 mL water was added. Water was added until cloudy and the solution was stored at 0° for 2 days. The solid was filtered, washed with 60° water, cold 50% aqueous MeOH, and dried (high-vacuum) to yield 14.0 g tan solid (41%); mp 107°–8°; $M^+242$.

EXAMPLE 3

3a,4,5,9b-Tetrahydro-6,7-dimethoxy-1H-benz[e]isoindole-1,3-(2H)-dione

A solution of the compound of example 2 (5.4 g, 22.3 mmole) and 55 mL methylene chloride was stirred at 0° as HBr(g) was bubbled through for 2 hours. The solution was stirred at 0° for an additional 1 hour without bubbling HBr. The solution was evaporated to dryness to obtain an orange glass which was dried briefly (in-vacuo), then a $N_2$ purged solution of 50 mL water/25 mL DMF was added. The black solution was heated on the steam bath for 2 hours and was allowed to stand overnight at room temperature. The precipitate was filtered, washed with cold 75/25; water/EtOH, then dried (in-vacuo) to yield 3.2 g brown needles (55%); $M^+261$; mp 217°–19°.

EXAMPLE 4

2-Ethyl-3a,4,5,9b-tetrahydro-6,7-dimethoxy-1H-benz[e]isoindole-1,3-(2H)-dione

A solution of thee compound of example 3 (1.5 g, 5.8 mmole), absolute ethanol (0.42 mL, 7.3 mmole), triphenylphosphine (1.5 g, 5.8 mmole), and dry THF (9.8 mL) was stirred under $N_2$ at 15° C. as diethyl azodicarboxylate (0.92 mL, 5.8 mmole) was added dropwise. The reaction mixture was stirred at room temperature for 18 hrs., then the crude reaction mixture was chromatographed on silica gel, eluting with $CH_2Cl_2$ containing 0.5% EtOH to obtain 0.96 g yellow solid (57%); $M^+289$.

EXAMPLE 5

2,3,3a,4,5,9b-Hexahydro-6,7-dimethoxy-1H-benz[e]isoindole hydrochloride

To a 0° slurry of the compound of example 3 (1.0 g, 3.8 mmole) and 10 mL dry THF was added $BH_3 \cdot THF$ (30.4 mL, 1M solution). The reaction mixture was stirred at reflux for 2 hours, then was cooled to 0° and excess methanolic HCl was added dropwise. The mixture was stirred at reflux for 0.5 hr, then overnight at room temperature. The solution was evaporated to dryness and water was added. Two $CH_2Cl_2$ extracts were combined and set aside. The aqueous layer was basified (KOH/water) and extracted three times with $CH_2Cl_2$. The combined basic extracts were washed with water, saturated aqueous NaCl, dried ($MgSO_4$), filtered, and evaporated to yield 0.7 g yellow oil (79%). The free base was converted to the HCl salt by dissolving in MeOH and adding ethereal HCl. Evaporation and drying (in-vacuo) afforded a white solid; mp 141°–3°; $M^+233$.

EXAMPLE 6

2-Ethyl-2,3,3a,4,5,9b-hexahydro-6,7-dimethoxy-1H-benz[e]isoindole hydrochloride

The compound of example 4 was reduced by the method of example 5; $M^+261$; mp 154°–8° C.

EXAMPLE 7

2-Ethyl-2,3,3a,4,5,9b-hexahydro-6,7-dihydroxy-1H-benz[e]isoindole hydrobromide A solution of the compound of example 6 (1.1 g, 3.7 mmole) and 11 mL CH$_2$Cl$_2$ was stirred under N$_2$ at −78° C. and a solution of BBr$_3$ (1.08 mL, 11.5 mmole) in 3.5 mL CH$_2$Cl$_2$ was added dropwise. The reaction mixture was stirred for 1 hr at −78°, 2 hours at 0°, and 1 hour at room temperature. After cooling again to −78°, 20 mL MeOH was added dropwise. The reaction mixture was allowed to slowly warm to room temperature overnight. Approximately 20 mL Et$_2$O was added and the precipitate filtered, washed with 5% EtOH in Et$_2$O, and dried (in-vacuo) to yield 0.8 g pale yellow solid; M+233; mp 223°-7°.

EXAMPLE 8

2-n-Propyl-2,3,3a,4,5,9b-hexahydro-6,7-dimethoxy-1H-benz[e]isoindole hydrochloride A slurry of NaH (0.68 g, 50% in oil, 14.1 mmole, washed 3 times with hexane) and 68 mL dry DMF was stirred under N$_2$ at room temperature as a solution of the compound of example 5 (free base) (3.0 g, 12.9 mmole) in 20 mL dry DMF was added dropwise. The reaction mixture was stirred for 1.5 hr. at room temperature, then 1-bromopropane (1.3 mL, 14.1 mmole) was added dropwise. The reaction mixture was stirred for 1 hr at room temperature, and for 18 hrs. at 30°-35° C. The reaction mixture was evaporated to dryness, water was added and the solution was extracted 3 times with CH$_2$Cl$_2$. The combined CH$_2$Cl$_2$ layers were washed with water, brine, dried (MgSO$_4$), filtered, evaporated, and converted to the HCl salt to yield 2.0 g (50%) gray glass; M+246.

EXAMPLE 9

2,3,3a,4,5,9b-Hexahydro-6,7-dihydroxy-2-n-propyl-1H-benz[e]isoindole hydrobromide The compound of example 8 was cleaved by the method of example 7; mp 228°-30°; M+247.

EXAMPLE 10

2-[2'(S)-(1',4'-Benzodioxan-2'-methyl)]-2,3,3a,4,5,9b-hexahydro-6,7-dimethoxy-1H-benz[e]isoindole hydrochloride A solution of the compound of example 5 (3.1 g, 13.3 mmole, free base), [2R[-2-tosyloxymethyl-1,4-benzodioxan (5.25 g, 16.4 mmole), N,N-diisopropylethylamine (19.3 mL), and CH$_3$CN (19.3 mL) was stirred at reflux for 16 hours. After cooling to room temperature the reaction mixture was evaporated (in-vacuo). Methylcyclohexane was added and evaporated twice. 1N KOH was added and the mixture was extracted 3 times with Et$_2$O. The combined extracts were washed with brine, dried (MgSO$_4$), filtered, and evaporated (in-vacuo) to obtain an oil which was converted to the HCl salt (MeOH/ethereal HCl). The crude product was crystallized from hot ethyl acetate to obtain 2.75 g (49%) tan solid; M+381; mp 207°-212°.

EXAMPLE 11

2-Allyl-3a,4,5,9b-tetrahydro-6,7-dimethoxy-1H-benz[e]isoindole-1,3-(2H)-dione A solution of the compound of example 3 (2.0 g, 7.36 mmole) and 34 mL dry DMF was stirred under N$_2$ at 0° C. as a suspension of NaH (60% in oil, 0.3 g, 7.5 mmole, washed with hexane) and 3.4 mL dry DMF was added portionwise. The Na salt was formed over ½ hr at 0° and ½ hr at room temperature. After cooling again to 0°, allyl bromide (0.67 mL, 8.0 mmole) was added dropwise. The reaction mixture was stirred for ½ hr. at 0° and for 1 hour at room temperature, and then was poured onto ice water with rapid stirring. The solid was filtered, washed with water, dried (in-vacuo) to yield 1.91 g cream colored solid (86%); mp 147°-8°.

EXAMPLE 12

2-Allyl-2,3,3a,4,5,9b-hexahydro-6,7-dimethoxy-1H-benz[e]isoindole hydrochloride A suspension of LAH (0.60 g, 15.8 mmole) in 10 mL dry Et$_2$O was stirred under N$_2$ at room temperature as a solution of the compound of example 11 (1.9 g, 6.3 mmole) and 15 mL dry Et$_2$O and 15 mL dry THF was added slowly. The reaction mixture was stirred at reflux for 3 hours. After cooling to 0° C. the following sequence was added: 0.6 mL water, 0.6 mL 15% aqueous NaOH, 1.8 mL water. The slurry was stirred for 1.5 hr, then filtered through Celite. The filtrate was dried (MgSO$_4$), filtered, evaporated, and converted to the HCl salt to obtain 1.7 g brown glass which was recrystallized from CH$_3$CN/Et$_2$O to yield 1.43 g gray powder (73%); mp 125°-9°; M+273.

EXAMPLE 13

2-Allyl-2,3,3a,4,5,9b-hexahydro-6,7-dihydroxy-1H-benz[e]isoindole hydrobromide The compound of example 12 was cleaved using the method of example 7; mp 203°-4° C.; M+245.

EXAMPLE 14

2-[3-(4-nitrophenyl)-propanoyl]-2,3,3a,4,5,9b-hexahydro-6,7-dimethoxy-1H-benz[e]isoindole A slurry of p-nitrocinnamic acid (1.9 g, 9.8 mmole, Aldrich) and 22 mL dry benzene was stirred under N$_2$ at 0° C. as oxalyl chloride (2.2 mL, 25.2 mmole) was added dropwise. The reaction mixture was stirred at reflux for 1¼ hr, was cooled to room temperature and evaporated. Benzene was added and evaporated several times. The acid chloride was dissolved in ca 15 mL CH$_2$Cl$_2$, and was added dropwise to a 0° C. solution of the compound of example 5 (free base, 1.9 g, 8.2 mmole) in 25 mL CH$_2$Cl$_2$, and triethylamine (1.6 mL, 11.5 mmole). The reaction mixture was stirred at room temperature for 1 hour. Water was added to the reaction mixture and the layers were separated. The aqueous layer was extracted twice with CH$_2$Cl$_2$. The combined organic layers were washed with 1N HCl, saturated aqueous NaHCO$_3$, saturated aqueous NaCl, dried (MgSO$_4$), filtered, and evaporated (in-vacuo) to yield a tan solid which was triturated with Et$_2$O to yield 2.68 g tan solid (80%); mp 231°-4°.

EXAMPLE 15

2-[3-(4-Aminophenyl)-propanoyl]-2,3,3a,4,5,9b-hexahydro-6,7-dimethoxy-1H-benz[e]isoindole A mixture of the compound of example 14 (1.83 g, 4.5 mmole), 2 g of Raney Nickel, and 250 mL of 2-methoxyethanol was hydrogenated at 3 atmospheres in a Parr shaker for 0.5 hour. The resulting mixture was filtered and evaporated to give 1.8 g (71%) as a brown oil; M+380.

EXAMPLE 16

2-[3-(4-Aminophenyl)-propyl]-2,3,3a,4,5,9b-hexahydro-6,7-dimethoxy-1H-benz[e]isoindole dihydrochloride A suspension of the compound of example 15 (2.6 g, 6.8 mmole) in 35 mL dry THF was stirred under $N_2$ at room temperature as $BH_3.THF$ (1M solution, 26.7 mL) was added. The reaction mixture was stirred at reflux for 2½ hrs. After cooling to 0° C., 30 mL methanolic HCl was added. The reaction mixture was stirred at reflux for 6 hours and at room temperature for 18 hours. The solution was evaporated (in vacuo) to dryness and water was added. After two neutral $Et_2O$ extracts, the aqueous layers were basified with 1N KOH and extracted three times with $CH_2Cl_2$. The combined basic extracts were washed with water, saturated aqueous NaCl, dried ($MgSO_4$), filtered, evaporated, converted to the HCl salt, and dried (in-vacuo) to obtain a gray foam which was crystallized from $Et_2O$/EtOH to yield 1.71 g white solid (57%); mp 233°–5° C.; $M^+366$.

EXAMPLE 17

2-[3-(4-Aminophenyl)-propyl]-2,3,3a,4,5,9b-hexahydro-6,7-dihydroxy-1H-benz[e]isoindole dihydrobromide A solution of the compound of example 16 (0.41 g, 0.92 mmole) in $CH_2Cl_2$ (9.2 mL) was stirred under $N_2$ at −78° C. as a solution of $BBr_3$ (0.37 mL, 3.9 mmole) in 2.1 mL of $CH_2Cl_2$ was added dropwise. The reaction mixture was stirred for 1 hour at −78° C., 2¼ hr at 0°, and 2¾ hr at room temperature, then was cooled again to −78° as MeOH (7.3 mL) was added slowly. The reaction mixture was allowed to warm to room temperature overnight. The precipitate was filtered, washed with $Et_2O$, and dried (in-vacuo) to yield 0.30 g light yellow powder; mp 290°; $M^+338$.

EXAMPLE 18

1-Cyano-6-methoxy-3,4-dihydronaphthalene

The compound was prepared from 6-methoxy-1-tetralone using the method of example 1.

EXAMPLE 19

1,2-Dicyano-6-methoxytetralin

The compound of example 18 was treated under the conditions of example 2; $M^+212$.

EXAMPLE 20

3a,4,5,9b-Tetrahydro-7-methoxy-1H-benz[e]isoindole-1,3-(2H)-dione

The compound of example 19 was treated under the conditions of example 3; $M^+231$.

EXAMPLE 21

2,3,3a,4,5,9b-Hexahydro-7-methoxy-1H-benz[e]isoindole hydrochloride $BH_3.THF$ (1M solution, 52 mL) was added to the compound of example 20 (1.5 g, 6.5 mmole). The reaction mixture was stirred at reflux for 2 hrs., cooled to 0°, and 10 mL 6N HCl added. After 2 hours reflux, solvents were evaporated. $CH_3CN$ was added and evaporated several times. The residue was crystallized from MeOH/$Et_2O$ to obtain 1.0 g white solid; $M^+203$.

EXAMPLE 22

2,3,3a,4,5,9b-Hexahydro-7-hydroxy-1H-benz[e]isoindole hydrobromide

Same reaction procedure as described for example 7, using the compound of example 21 as starting material; mp 250° C.; $M^+189$.

EXAMPLE 23

2-[2'(S)-(1',4'-Benzodioxan-2'-methyl)]-2,3,3a,4,5,9b-hexahydro-7-methoxy-1H-benz[e]isoindole hydrochloride The reaction procedure described for example 10 was repeated, using the compound of example 21 as starting material; mp 179°–81° C.

EXAMPLE 24

1-Cyano-5-methoxy-3,4-dihydronaphthalene

A solution of 5-methoxy-1-tetralone (52.0 g, 0.29 mole, Aldrich), TMSCN (51 mL, 0.38 mole, Aldrich), 40 mL dry benzene, and catalytic $AlCl_3$ was stirred under $N_2$ at 65° C. for 1 hour. The reaction mixture was cooled and evaporated to dryness. To the residue was added 300 mL pyridine and $POCl_3$ (80 mL, 0.88 mole). The reaction mixture was stirred at reflux for 2 hours, then was cooled to room temperature and was poured onto ice/concentrated HCl. A precipitate was collected, washed with water, and purified by column chromatography (silica gel/$CH_2Cl_2$) to obtain 54 g (73%); $M^+185$.

EXAMPLE 25

1,2-Dicyano-5-methoxytetralin

Using the method of example 2 with the compound of example 24 as the starting material gave the above named compound; $M^+212$.

EXAMPLE 26

3a,4,5,9b-Tetrahydro-6-methoxy-1H-benz[e]isoindole-1,3-(2H)-dione

The method of example 3 was used to transform the compound of example 25 to the desired product; $M^+231$.

EXAMPLE 27

2,3,3a,4,5,9b-Hexahydro-6-methoxy-1H-benz[e]isoindole hydrochloride

The method of example 5 was used to transform the compound of example 26 to the desired product; mp 215°–16° C.

EXAMPLE 28

2-[2'(R,S)-(1',4'-benzodioxan-2'methyl)]-2,3,3a,4,5,9b-hexahydro-6-methoxy-1H-benz[e]isoindole hydrochloride Using the same reaction procedure as described for example 10, but starting with the product of example 27 afforded the desired product; $M^+349$; mp 175°–8°.

EXAMPLE 29

2,3,3a,4,5,9b-Hexahydro-6-hydroxy-1H-benz[e]isoindole hydrobromide

Using the procedure as described for example 7, but starting with the product of example 27 afforded the desired product; M+189; mp 270° C.

EXAMPLE 30

3a,4,5,9b-Tetrahydro-6-methoxy-2-methyl-1H-benz[e]isoindole-1,3-(2H)-dione

A suspension of NaH (50% in oil, 0.65 g, 13.5 mmole) and 50 mL dry DMF was stirred at room temperature as a solution of the product of example 26 (3.0 g, 13.0 mmole) and 5 mL dry DMF was added dropwise. The reaction mixture was stirred at room temperature for 1.5 hour. Dimethylsulfate (1.3 mL, 13.5 mmole) was added dropwise. After stirring for 0.5 hour at room temperature, the reaction mixture was poured onto ice/water and was extracted with $CH_2Cl_2$. The $CH_2Cl_2$ layers were washed well with water, saturated aqueous NaCl, dried ($MgSO_4$), filtered, and evaporated (in-vacuo) to yield 1.70 g yellow oil; (55%); M+245.

EXAMPLE 31

2,3,3a,4,5,9b-Hexahydro-6-methoxy-2-methyl-1H-benz[e]-isoindole hydrochloride

Using the procedure described for example 5, but starting with the product of example 30 afforded the desired compound; M+217; mp 214°-5°.

EXAMPLE 32

2,3,3a,4,5,9b-Hexahydro-6-hydroxy-2-methyl-1H-benz[e]isoindole hydrobromide

Using the procedure of example 7, but starting with the product of example 31 afforded the desired product; M+203; mp 226°-7°.

EXAMPLE 33

2,3,3a,4,5,9b-Hexahydro-6-methoxy-2-(2-methoxyphenoxy)acetyl-1H-benz[e]isoindole Using the procedure described in example 14, but starting with the product of example 27 and o-methoxyphenoxyacetic acid afforded the desired compound, (86%).

EXAMPLE 34

2,3,3a,4,5,9b-Hexahydro-6-methoxy-2[2'-(2-methoxyphenoxy)ethyl]-1H-benz[e]isoindole hydrochloride Using the procedure as described for example 16, but starting with the product of example 33 afforded the desired compound; M+353.

EXAMPLE 35

2-Formyl-6-methoxyphenylmethylcarbonate

A solution of o-vanillin (125 g, 0.81 mole), 1250 mL benzene, and 118 mL triethylamine was stirred under $N_2$ at 0° as methylchloroformate (82 mL, 1.06 mole) was added over 1 hour. The reaction mixture was stirred at room temperature for 3 hours, then was poured onto water and the layers were separated. The aqueous layer was extracted with benzene. The combined organic layers were washed with water, 10% HCl, saturated aqueous NaCl dried ($MgSO_4$), filtered, evaporated, and dried (in-vacuo) to yield 170 g light yellow solid; mp 52°-4°.

EXAMPLE 36

3-Bromo-2-formyl-6-methoxyphenylmethylcarbonate

A solution of 2-formyl-6-methoxyphenylmethylcarbonate (170 g, 0.81 mole), NaOAc (66 g, anhydrous), Fe powder (0.52 g), and glacial acetic acid (1600 mL) was stirred under $N_2$ at room temperature as bromine (60 mL, 1.17 mole) was added dropwise over 1 hour. The reaction mixture was stirred at room temperature for 5 hours. More bromine was added portionwise over 2 days until the reaction was complete. The reaction mixture was poured onto ice with stirring. The solid was filtered, washed with water, and dried (in-vacuo) to yield 200 g red powder which was recrystallized from 2-propanol to yield 92 g white powder; mp 115°-20°; M+288.

EXAMPLE 37

6-Bromo-2-hydroxy-3-methoxybenzaldehyde

A solution of 3-bromo-2-formyl-6-methoxyphenylmethyl carbonate (100 g, 0.34 mole), 500 mL 10% aqueous NaOH, and 2 L MeOH was stirred at reflux for 2 hours. After cooling to room temperature, the MeOH was removed (in-vacuo). The aqueous solution was cooled to 0° and acidified with concentrated HCl. The solid was filtered, washed with water, and dried (in-vacuo) to yield 107 g yellow solid which was recrystallized from 2-propanol to yield 62 g yellow solid; mp 95°-6°; M+230.

EXAMPLE 38

6-Bromo-2,3-dimethoxybenzaldehyde

A mixture of 6-bromo-2-hydroxy-3-methoxybenzaldehyde (66.8 g, 0.29 mole), $K_2CO_3$ (powdered, 79 g, 0.57 mole), and dry DMF (250 mL) was stirred under $N_2$ at 110° as dimethylsulfate (33.5 mL, 0.35 mole) was added dropwise. The reaction mixture was stirred at 135° for 5 hours, was cooled to room temperature, and water was added. The aqueous mixture was extracted with $CH_2Cl_2$. The combined extracts were washed with water, saturated aqueous NaCl, dried ($MgSO_4$), filtered, and evaporated to yield ca 80 g. tan solid. The crude product was recrystallized from 2-propanol to obtain 55.2 g cream colored solid, (77%); mp 92°-3°.

EXAMPLE 39

α-Cyano-6-bromo-2,3-dimethoxycinnamic acid

A mixture of 6-bromo-2,3-dimethoxybenzaldehyde (48.4 g, 0.20 mole), $NH_4OAc$ (1.93 g, 0.025 mole), cyanoacetic acid (0.186 mole, 15.8 g), pyridine (42 mL), and benzene (193 mL) was stirred at reflux for 2 hours using a Dean-Stark trap for water removal. Upon cooling to room temperature a solid was filtered and washed with hexane. The solid was dissolved in 1N KOH, and was extracted with ether. The aqueous layer was acidified with 10% HCl and was extracted with $CH_2Cl_2$. The combined $CH_2Cl_2$ layers were washed with water, saturated aqueous NaCl, dried ($MgSO_4$), filtered, and evaporated to yield 41.7 g yellow solid, (67%); mp 130°-2°; M+311.

EXAMPLE 40

2-Cyano-3-(6-bromo-2,3-dimethoxyphenyl)-propionic acid

A solution of α-cyano-6-bromo-2,3-dimethoxycinnamic acid (41.7 g, 0.13 mole), and absolute EtOH (1 L) was stirred under $N_2$ at 0° as $NaBH_4$ (42 g. 1.11 mole) was added portionwise. The reaction mixture was stirred at room temperature for 0.5 hr., and at reflux for 0.75 hr. After cooling to room temperature, EtOH was removed (in-vacuo). Water was added to the residue, followed by 10% HCl until acidic. The solution was extracted with $CH_2Cl_2$. The combined organic layers were washed with water, saturated aqueous NaCl, dried ($MgSO_4$), filtered, and evaporated to yield 39.25 g cream colored solid; mp 120°-2°; M+313.

EXAMPLE 41

3-(6-Bromo-2,3-dimethoxyphenyl)-propionitrile

A solution of 2-cyano-3-(6-bromo-2,3-dimethoxyphenyl)-propionic acid (39.25 g, 0.125 mole), and 80 mL N,N-dimethylacetamide was stirred at 160° for 1.25 hr. After cooling to room temperature, the solution was poured onto ice with stirring. The solid was filtered, washed with water, dried (in-vacuo) to yield 32.7 g white solid, (97%); M+269.

EXAMPLE 42

1,2-Dihydro-3,4-dimethoxybenzocyclobutene-1-carbonitrile

A mixture of liquid $NH_3$ (400 mL) and catalytic Fe(-$NO_3)_3$ was stirred under $N_2$ at −50° C. A small portion of Na metal (from a total amount of 20 g., 0.87 mole) was added. Air was bubbled through the reaction mixture briefly until a black precipitate appeared. The remaining Na was added portionwise. 3-(6-bromo-2,3-dimethoxyphenyl)-propionitrile (31.1 g, 0.115 mole) was added over 70 minutes as the reaction mixture was stirred at slow reflux. When the addition was complete, the reaction mixture was stirred at reflux for ½ hr, then was cooled to −55° C. as $NH_4Cl$ (35.2 g, 0.66 mole) was added slowly. $NH_3$ was allowed to evaporate overnight. Water was added cautiously with stirring. The solid was filtered, washed with water, dried (in-vacuo) to yield 21.0 g gray powder, (97%); M+189.

EXAMPLE 43

3,4-Dimethoxybenzocyclobutene-1-carboxylic acid

A mixture of 1,2-dihydro-3,4-dimethoxybenzocyclobutene-1-carbonitrile (21.9 g, 0.12 mole) and EtOH saturated with KOH (45 g/200 mL) was stirred at reflux for 2 hours. After cooling to room temperature EtOH was removed (in-vacuo) and water was added. The aqueous layer was extracted with ether, then was acidified with concentrated HCl and was extracted with $CH_2Cl_2$. The combined acidic extracts were washed with water, saturated aqueous NaCl, dried ($MgSO_4$), filtered, and evaporated to yield 19.8 g brown solid which was recrystallized from benzene to yield 19.7 g white powder, (82%); mp 112°-14°; M+208.

EXAMPLE 44

3,4-Dimethoxy-N-(2-propenyl)-benzocyclobutene-1-carboxamide

A solution of 3,4-dimethoxybenzocyclobutene-1-carboxylic acid and 400 mL benzene was stirred under $N_2$ at 0° as oxalyl chloride (40.6 mL, 0.47 mole) was added dropwise. The reaction mixture was stirred for 2 hours at room temperature, then solvents were evaporated. Benzene was added and evaporated. The acid chloride was dissolved in $CH_2Cl_2$ (200 mL) and was added dropwise to a stirred, 0° solution of allylamine (8.5 mL, 0.11 mole), triethylamine (59 mL), and $CH_2Cl_2$ (212 mL). The reaction mixture was stirred for 1 hour at room temperature, then water was added. The layers were separated and the aqueous layer was extracted with $CH_2Cl_2$. The combined organic layers were washed with 1N HCl, saturated aqueous $NaHCO_3$, saturated aqueous NaCl, dried ($MgSO_4$), filtered, and evaporated (in-vacuo) to yield 19.8 g cream colored solid, (84%); mp 98°-9°; M+247.

EXAMPLE 45 trans-3a,4,5,9b-Tetrahydro-6,7-dimethoxy-1H-benz[e]isoindole-1-(2H)-one

A solution of 3,4-dimethoxy-N-(2-propenyl)benzocyclobutene-1-carboxamide (13.2 g, 0.053 mole) and o-dichlorobenzene (600 mL) was stirred at reflux for 15 hours. After cooling to 0°, a solid was filtered, washed with hexane, and dried (in-vacuo) to yield 6.8 g white solid. cis And trans isomers were separated by HPLC to obtain: 1.80 g trans isomer; mp 185°-7°; M+247; and 3.50 g cis isomer; mp 219°-21°; M+247.

EXAMPLE 46 trans-2,3,3a,4,5,9b-Hexahydro-6,7-dimethoxy-1H-benz[e]isoindole hydrochloride

A solution of trans-3a,4,5,9b-tetrahydro-6,7-dimethoxy-1H-benz[e]isoindole-1-(2H)-one and 15 mL dry THF was stirred under $N_2$ at 0° as $BH_3$.THF (27.3 mL, 1M solution) was added slowly. The reaction mixture was stirred at reflux for 2.5 hours, was cooled to 0°, and 30 mL methanolic HCl was added cautiously. The solution was stirred at reflux for 1 hour, then was evaporated to dryness. Water was added and the aqueous layer was extracted with ether. After basifying (1N KOH), the aqueous layer was extracted with ether. The combined basic extracts were washed with water, saturated aqueous NaCl, dried ($MgSO_4$), filtered, and evaporated to yield a clear oil which was converted to the HCl salt (ethereal HCl), evaporated, dried (in-vacuo) to obtain a white solid which was triturated with ether to yield 1.03 g cream colored solid, (63%); mp 196°-8°; M+233.

EXAMPLE 47 trans-2,3,3a,4,5,9b-Hexahydro-6,7-dihydroxy-1H-benz[e]isoindole hydrobromide

Using the procedure as described for example 7, but starting with the product from example 46 afforded the desired compound; mp 295°; M+205.

EXAMPLE 48 trans-2,3,3a,4,5,9b-Hexahydro-6,7-dimethoxy-2-methyl-1H-benz[e]isoindole hydrochloride A solution of the product of example 46, formalin (5 mL), NaOAc.3$H_2O$ (0.45 g), and MeOH (95 mL) in the presence of Pd/C catalyst (0.45 g, 5%, wet) was hydrogenated under 3 atmospheres $H_2$ pressure. The resulting solution was filtered and evaporated to dryness. Water/1N KOH were added and the solution was extracted with ether. The combined extracts were washed with water, saturated aqueous NaCl, dried (MgSO$_4$), filtered, evaporated, and converted to the HCl salt. The crude product was triturated with ether/MeOH, filtered, and dried to yield 0.70 g gray powder, (75%); mp 228°–30° C.; M+247.

EXAMPLE 49 trans-2,3,3a,4,5,9b-Hexahydro-6,7-dihydroxy-2-methyl-1H-benz[e]isoindole hydrochloride Using the procedure as described in example 7, but starting with the product from example 48 afforded the desired compound; mp 280°; M+219.

EXAMPLE 50 trans-2-Acetyl-2,3,3a,4,5,9b-hexahydro-6,7-dimethoxy-1H-benz[e]isoindole

A solution of trans-2,3,3a,4,5,9b-hexahydro-6,7-dimethoxy-1H-benz[e]isoindole hydrochloride (0.50 g, 1.9 mmole) and dry pyridine (9.5 mL) was stirred under N$_2$ at room temperature as acetic anhydride (0.26 mL, 2.8 mmole) was added dropwise. The reaction mixture was stirred at room temperature for 0.75 hr, then was evaporated (in-vacuo). 2-Methoxyethanol was added and evaporated. The residue was dissolved in CH$_2$Cl$_2$ and was washed with 1N HCl, 1N KOH, water, saturated aqueous NaCl, dried (MgSO$_4$), filtered and evaporated to yield 0.60 g white solid; M+275.

EXAMPLE 51 trans-2-Ethyl-2,3,3a,4,5,9b-hexahydro-6,7-dimethoxy-1H-benz[e]isoindole hydrochloride Using the procedure as described for example 16, but starting with the product from example 50 afforded the desired compound; M+261.

EXAMPLE 52 trans-2-Ethyl-2,3,3a,4,5,9b-hexahydro-6,7-dihydroxy-1H-benz[e]isoindole hydrobromide Using the procedure as described for example 7, but starting with the product from example 51 afforded the desired compound; mp 280°; M+233.

EXAMPLE 53

Ethyl-4-keto-γ-(2-methoxy-5-methylphenyl)-butyrate

A solution of p-methylanisole (100 g, 0.81 mole), β-carbethoxypropionylchloride (96%, 230 g, 1.22 mole), and CH$_2$Cl$_2$ (800 mL) was stirred under N$_2$ at 0° as AlCl$_3$ (131 g, 0.94 mole) was added over 2 hours. The reaction mixture was stirred at room temperature for 20 hours, then was poured onto ice and the layers were separated. The aqueous layer was extracted with CH$_2$Cl$_2$. The combined organic layers were washed with water, saturated aqueous NaHCO$_3$, 1N KOH, H$_2$O, saturated aqueous NaCl, dried (MgSO4), filtered, and evaporated (in-vacuo) to obtain a yellow oil.

EXAMPLE 54

4-Keto-γ-(2-methoxy-5-methylphenyl)-butyric acid

A solution of ethyl-4-keto-γ-(2-methoxy-5-methylphenyl)-butyrate (180 g, 0.81 mole) and 1200 mL 20% NaOH was stirred at reflux for 3 hours. After cooling to 0°, the solution was acidified with concentrated HCl. The solid was filtered, washed with water, dried (in-vacuo) to yield 145 g orange solid. Recrystallization from CCl$_4$ yielded 123 g light yellow powder, (68%).

EXAMPLE 55

4-(2-Methoxy-5-methylphenyl)-butyric acid

A mixture of 4-Keto-γ-(2-methoxy-5-methylphenyl)-butyric acid (123 g, 0.55 mole), HOAc (1.5 L), and H$_2$SO$_4$ (3.2 mL) in the presence of Pd/C catalyst (12.2 g, dry) was hydrogenated under 3 atmospheres H$_2$ pressure for 3 hours at room temperature. The resulting solution was filtered and was evaporated to the volume of 100 mL. Water (1000 mL) was added with stirring. The solid was filtered, dried (in-vacuo), and was recrystallized from ether/hexane to yield 74 g white solid, (64%); m+208.

EXAMPLE 56

4-(3-Bromo-2-methoxy-5-methylphenyl)-butyric acid

A solution of 4-(2-methoxy-5-methylphenyl)-butyric acid (74 g, 0.36 mole), NaOAc (29.8 g, anhydrous), and glacial acetic acid (710 mL) was stirred under N$_2$ at room temperature, as a solution of bromine (22 mL, 0.43 mole) and glacial acetic acid (185 mL) was added dropwise. The reaction mixture was stirred at room temperature for 20 hours. 10% aqueous sodium bisulfite (400 mL) was added and the solution was extracted with CH$_2$Cl$_2$. The combined extracts were washed with water, 10% aqueous sodium thiosulfate, water, saturated aqueous. NaCl, dried (MgSO4), filtered, and evaporated to yield 108 g brown solid which was recrystallized from hexane to yield 76 g white solid, (74%); m+286.

EXAMPLE 57

4-(2,3-Dimethoxy-5-methylphenyl)-butyric acid

Sodium methoxide was prepared by adding sodium metal (27 g, 1.16 mole) slowly to MeOH (450 mL). The methanol was evaporated (in-vacuo) and the sodium methoxide was dried (in-vacuo). The following was then added: 4-(3-bromo-2-methoxy-5-methylphenyl)-butyric acid (53.9 g, 0.19 mole), CuI (5.4 g), DMF (270 mL). The reaction mixture was stirred at 80° for 7 hours and 18 hours at room temperature. Water was added and the reaction mixture was evaporated to dryness. More water was added and the solution was extracted with ether. The aqueous layer was acidified with 6N HCl and was extracted with CH$_2$Cl$_2$. The extracts were washed with 1N HCl, water, saturated aqueous NaCl, dried (MgSO$_4$), filtered, and evaporated to yield 44 g black oil, (97%); M+238.

EXAMPLE 58

5,6-Dimethoxy-8-methyl-1-tetralone

A mixture of 4-(2,3-dimethoxy-5-methylphenyl)-butyric acid (50.7 g, 0.21 mole) and methanesulfonic acid (507 g, 355 mL) was stirred at 0° for 1 hour and overnight at room temperature. The reaction mixture was poured onto ice, and the solution was extracted with CH$_2$Cl$_2$. The combined CH$_2$Cl$_2$ layers were washed with 1N KOH, water, saturated aqueous NaCl, dried (MgSO$_4$), filtered, and evaporated to yield 20.2 g tan solid, (44%); mp 58°–62°; M+204.

EXAMPLE 59

1-Cyano-3,4-dihydro-5,6-dimethoxy-8-methylnaphthalene

Using the procedure of Example 1, and the product from Example 58 gave the compound; M+229.

EXAMPLE 60

1,2-Dicyano-5,6-dimethoxy-8-methyl-1-tetralone

Using the procedure as described for Example 2, but starting with 1-cyano-3,4-dihydro-5,6-dimethoxy-8-methylnaphthalene, afforded the desired compound, M+256.

EXAMPLE 61

3a,4,5,9b-Tetrahydro-6,7-dimethoxy-9-methyl-1H-benz[e]isoindole-1,3-(2H)-dione

Using the procedure as described for Example 3 but starting with 1,2-dicyano-5,6-dimethoxy-8-methyltetralin, afforded the desired compound; M+275; mp 179°–81°.

EXAMPLE 62

2,3,3a,4,5,9b-Hexahydro-6,7-dimethoxy-9-methyl-1H-benz[e]isoindole hydrochloride Using the procedure as described for Example 5, but starting with 3a,4,5,9b-tetrahydro-6,7-dimethoxy-9-methyl-1H-benz[e]isoindole-1,3-(2H)-dione, afforded the desired compound; M+247; mp 186°–90°.

EXAMPLE 63

2,3,3a,4,5,9b-Hexahydro-6,7-dihydroxy-9-methyl-1H-benz[e]isoindole hydrobromide

Using the procedure same as described for Example 7, but starting with 2,3,3a,4,5,9b-hexahydro-6,7-dimethoxy-9-methyl-1H-benz[e]isoindole hydrochloride, afforded the desired compound; M+219; m.p. 214°–16° C.

EXAMPLE 64

3a,4,5,9b-Tetrahydro-6,7-dimethoxy-2,9-dimethyl-1H-benz[e]isoindole-1,3-(2H)-dione A solution of 3a,4,5,9b-tetrahydro-6,7-dimethoxy-9-methyl-1H-benz[e]isoindole-1,3-(2H)-dione (1.66 g, 6.1 mmole) and dry DMF (28 mL) was stirred under $N_2$ at 0° as a suspension of NaH (60% in oil, washed with hexane, 0.25 g, 6.4 mmole) and DMF (2.8 mL) was added portionwise. The reaction mixture was stirred for 0.5 hour at 0°, and for 0.5 hour at room temperature, then was cooled again at 0° as methyliodide (9.41 mL, 6.6 mmole) was added dropwise. After one hour at 0° and 1.5 hours at room temperature, the reaction mixture was poured onto ice water. The solid was filtered, washed with water, dried (in vacuo) to yield 1.60 g yellow solid (91%), mp 167°–9° C.; M+289.

EXAMPLE 65

2,3,3a,4,5,9b-Hexahydro-6,7-dimethoxy-2,9-dimethyl-1H-benz[e]isoindole hydrochloride Using the procedure as described for Example 5 but starting with 3a,4,5,9b-tetrahydro-6,7-dimethoxy-2,9-dimethyl-1H-benz[e]isoindole-1,3-(2H)-dione, afforded the desired compound, mp 218°–21° C.; M+261.

EXAMPLE 66

2,3,3a,4,5,9b-Hexahydro-6,7-dihydroxy-2,9-dimethyl-1H-benz[e]isoindole hydrobromide Using the procedure as described for Example 7 but starting with 2,3,3,a,4,5,9b-hexahydro-6,7-dimethoxy-2,9-dimethyl-1H-benz[e]isoindole hydrochloride, afforded the desired compound; M+233; mp 205°–11° C.

EXAMPLE 67

2-Allyl-3a,4,5,9b-tetrahydro-6,7-dimethoxy-9-methyl-1H-benz[e]isoindole-1,3-(2H)-dione Using the procedure as described for Example 11, but starting with 3a,4,5,9b-tetrahydro-6,7-dimethoxy-9-methyl-1H-benz[e]isoindole-1,3-(2H)-dione, afforded the desired compound, M+315; mp 90°–1° C.

EXAMPLE 68

2-Allyl-2,3,3a,4,5,9b-hexahydro-6,7-dimethoxy-9-methyl-1H-benz[e]isoindole hydrochloride Using the procedure as described for Example 12, but starting with 2-allyl-3a,4,5,9b-tetrahydro-6,7-dimethoxy-9methyl-1H-benz[e]isoindole-1,3-(2H)-dione, afforded the desired compound; M+287; mp 206°–7° C.

EXAMPLE 69

2-Allyl-2,3,3a,4,5,9b-hexahydro-6,7-dihydroxy-9-methyl-1H-benz[e]isoindole hydrobromide Using the procedure as described for Example 7 but starting with 2-allyl-2,3,3a,4,5,9b-hexahydro-6,7-dimethoxy-9-methyl-1H-benz[e]isoindole hydrochloride, afforded the desired compound, M+259; mp 253°–4° C.

EXAMPLE 70

2-Ethyl-3a,4,5,9b-tetrahydro-6,7-dimethoxy-9-methyl-1H-benz[e]isoindole-1,3-(2H)dione Using the procedure as described for Example 64, but starting with 3,3a,4,5-tetrahydro-6,7-dimethoxy-9-methyl-1H-benz[e]isoindole-1,3-(2H)-dione, and using ethyl iodide in place of methyl iodide afforded the desired compound.

EXAMPLE 71

2-Ethyl-2,3,3a,4,5,9b-hexahydro-6,7-dimethoxy-9-methyl-1H-benz[e]isoindole hydrochloride Using the procedure as described for Example 5, but starting with 2-ethyl-3a,4,5,9b-tetrahydro-6,7-dimethoxy-9-methyl-1H-benz[e]isoindole-1,3-(2H)-dione, afforded the desired compound.

EXAMPLE 72

2-Ethyl-2,3,3a,4,5,9b-hexahydro-6,7-dihydroxy-9-methyl-1H-benz[e]-isoindole hydrobromide Using the procedure as described for Example 7, but starting with 2-ethyl-2,3,3a,4,5,9b-hexahydro-6,7-dimethoxy-9-methyl-1H-benz[e]isoindole hydrochloride, afforded the desired compound.

EXAMPLE 73

Ethyl-4-keto-γ-(5-ethyl-2-methoxyphenyl)butyrate

Using the procedure as described for Example 53 but starting with p-ethylanisole, afforded the desired compound, M+264.

EXAMPLE 74

Ethyl-4-(5-ethyl-2-methoxyphenyl)-butyrate

Using the procedure as described for Example 157, but starting with ethyl-4-keto-γ-(5-ethyl-2-methoxyphenyl)-butyrate afforded the desired compound.

EXAMPLE 75

4-(5-Ethyl-2-methoxyphenyl)-butyric acid

Using the procedure as described for Example 54, but starting with ethyl 4-(2-methoxy-5-ethylphenyl)-butyrate afforded the desired compound, M+222.

EXAMPLE 76

4-(3-Bromo-5-ethyl-2-methoxyphenyl)-butyric acid

Using the procedure as described for Example 56, but starting with 4-(2-methoxy-5-ethylphenyl)-butyric acid afforded the desired compound; M+300.

EXAMPLE 77

4-(5-Ethyl-2,3-dimethoxyphenyl)-butyric acid

Using the procedure as described for Example 57, but starting with 4-(3-bromo-2-methoxy-5-ethylphenyl)-butyric acid afforded the desired compound.

EXAMPLE 78

8-Ethyl-5,6-dimethoxy-α-tetralone

Using the procedure as described for Example 58, but starting with 4-(5-ethyl-2,3-dimethoxyphenyl)-butyric acid afforded the desired compound; M+234.

EXAMPLE 79

1-Cyano-8-ethyl-3,4-dihydro-5,6-dimethoxynaphthalene

Using the procedure as described for Example 1, but starting with 8-ethyl-5,6-dimethoxy-α-tetralone afforded the desired compound; M+243.

EXAMPLE 80

1,2-Dicyano-8-ethyl-5,6-dimethoxytetralin

Using the procedure as described for Example 2, but starting with 1-cyano-8-ethyl-3,4-dihydro-5-6-dimethoxynaphthalene afforded the desired compound; M+270.

EXAMPLE 81

9-Ethyl-3a,4,5,9b-tetrahydro-6,7-dimethoxy-1H-benz[e]isoindole-1,3-(2H)-dione

Using the procedure as described for Example 3, but starting with 1,2-dicyano-8-ethyl-5,6-dimethoxytetralin afforded the desired compound.

EXAMPLE 32

2,9-Diethyl-3a,4,5,9b-tetrahydro-6,7-dimethoxy-1H-benz[e]isoindole-1,3-(2H)-dione Using the procedure as in example 64, but starting with 9-ethyl-3a,4,5,9b-tetrahydro-6,7-dimethoxy-1H-benz[e]isoindole-1,3-(2H)-dione, and ethyl iodide in place of methyl iodide afforded the desired compound.

EXAMPLE 83

2,9-Diethyl-2,3,3a,4,5,9b-hexahydro-6,7-dimethoxy-1H-benz[e]isoindole hydrochloride Using the procedure as described for Example 5, but starting with 2,9-diethyl-3a,4,5,9b-tetrahydro-6,7-dimethoxy-1H-benz[e]isoindole-1,3-(2H)-dione afforded the desired compound.

EXAMPLE 84

2,9-Diethyl-2,3,3a,4,5,9b-hexahydro-6,7-dihydroxy-1H-benz[e]isoindole hydrobromide Using the procedure as described for Example 7, but starting with 2,9-diethyl-2,3,3a,4,5,9b-hexahydro-6,7-dimethoxy-1H-benz[e]isoindole hydrochloride afforded the desired compound.

EXAMPLE 85

2-Ethyl-2,3,3a,4,5,9b-hexahydro-6,7-dihydro-9-propyl-1H-benz[e]isoindole hydrobromide Using the procedure as described for example 7, but starting with 2-ethyl-2,3,3a,4,5,9b-hexahydro-6,7-dimethoxy-9-propyl-1H-benz[e]isoindole hydrochloride (prepared as described in examples 53–71, but starting with p-propylanisole) afforded the desired compound.

EXAMPLE 86

9-Butyl-2-ethyl-2,3,3a,4,5,9b-hexahydro-6,7-dihydroxy-1H-benz[e]isoindole hydrobromide Using the procedure as described for example 7, but starting with 9-butyl-2-ethyl-2,3,3a,4,5,9b-hexahydro-6,7-dimethoxy-1H-benz[e]isoindole hydrochloride (prepared as described in examples 53–71, but starting with p-butylanisole) afforded the desired compound.

EXAMPLE 87

6-Hydroxy-α-tetralone

A mixture of 6-methoxy-α-tetralone (30 g, 0.17 mole), $AlCl_3$ (45 g, 0.34 mole), and benzene (300 mL) was stirred at reflux for overnight. After cooling to room temperature, the reaction mixture was poured onto ice. The solid was filtered, washed with water, dried (in vacuo) to yield 22.3 g tan powder, (81%); M+162.

EXAMPLE 88

5-Bromo-6-hydroxy-α-tetralone

A solution of 6-hydroxy-α-tetralone (40.2 g, 0.25 mole), concentrated $H_2SO_4$ (375 mL), and $H_2O$ (375 mL) was stirred at 0° as N-bromosuccinimide (44.5 g, 0.25 mole) was added portionwise. The reaction mixture was stirred at room temperature for 2 hours. The solid was filtered, washed with water, dried (in-vacuo), and recrystallized from toluene to yield 24.8 g brown solid, (41%); mp 179°–83°.

EXAMPLE 89

5-Bromo-6-methoxy-α-tetralone

A mixture of 5-bromo-6-hydroxy-α-tetralone (23.6 g, 0.099 mole), $K_2CO_3$ (20.8 g, 0.15 mole), methyliodide (9.4 mL, 0.15 mole), and acetone (425 mL) was stirred at reflux for 8 hours. After cooling to room temperature, acetone was evaporated (in-vacuo) and water was added to the residue. The solution was extracted with $CH_2Cl_2$. The combined extracts were washed with water, 1N HCl, saturated aqueous NaCl, dried ($MgSO_4$), filtered, and evaporated (in-vacuo) to yield 20.85 g white solid, (83%); M+254; mp 97°–100°.

EXAMPLE 90

5-Bromo-1-cyano-3,4-dihydro-6-methoxynaphthalene

Using the procedure as described for example 1, but starting with 5-bromo-6-methoxy-α-tetralone afforded the desired compound; mp 108°–9°; M+263.

EXAMPLE 91

5-Bromo-1,2-dicyano-6-methoxytetralin

Using the procedure as described for example 2, but starting with 5-bromo-1-cyano-3,4-dihydro-6-methoxynaphthalene, afforded the desired compound; M+290.

EXAMPLE 92

6-Bromo-3a,4,5,9b-tetrahydro-7-methoxy-1H-benz-[e]isoindole-1,3-(2H)-dione

Using the procedure of example 3, but starting with the product of example 91 afforded the desired product; mp 243°–5°; M+309.

EXAMPLE 93

6-Bromo-2,3,3a,4,5,9b-hexahydro-7-methoxy-1H-benz[e]isoindole hydrochloride

Using the procedure of example 5, but starting with the product from example 92, afforded the desired compound; M+281; mp 204°–5°.

EXAMPLE 94

6-Bromo-2,3,3a,4,5,9b-hexahydro-7-hydroxy-1H-benz-[e]isoindole hydrobromide

Using the procedure of example 7, but starting with the product from example 93, afforded the desired compound; M+267; mp 261°–2° C.

EXAMPLE 95

6-Bromo-3a,4,5,9b-tetrahydro-7-methoxy-2-methyl-1H-benz[e]isoindole-1,3-(2H)-dione Using the procedure from example 64, but starting with the product from example 92 afforded the desired product; M+323; mp 196°–9° C.

EXAMPLE 96

6-Bromo-2,3,3a,5,6,9b-hexahydro-7-methoxy-2-methyl-1H-benz[e]isoindole hydrochloride Using the procedure of example 5, but starting with the product from example 95 afforded the desired product; M+295; mp 192°–5° C.

EXAMPLE 97

6-Bromo-2,3,3a,4,5,9b-hexahydro-7-hydroxy-2-methyl-1H-benz[e]isoindole hydrobromide Using the procedure of example 7, but starting with the product from example 96 afforded the desired compound; M+281; mp 70°–90° C.

EXAMPLE 98

Dihydro-m-methoxycinnamic acid

A mixture of m-methoxycinnamic acid (100 g, 0.56 mole), water (1 L), and NaOH (22.4 g, 0.56 mole), in the presence of Raney nickel catalyst (20 g, #30), was hydrogenated under 3 atmospheres $H_2$ pressure until the theoretical uptake of hydrogen was observed. The solution was filtered, cooled to 0°, and concentrated HCl was added until acidic pH was achieved. The solid was filtered, washed with water, dried (in-vacuo) to yield 90.6 g white solid, (90%); M+180.

EXAMPLE 99

3-(3-methoxyphenyl)-propanol

A solution of dihydro-m-methoxycinnamic acid (90 g, 0.5 mole) and tetrahydrofuran (250 mL) was stirred under $N_2$ at 0° as $BH_3.THF$ (1M solution, 525 mL) was added slowly. The reaction mixture was stirred at room temperature for 2 hours. After cooling to −5° C., 1N HCl was added. THF was evaporated and water was added to the residue. The aqueous layer was extracted with ether. The combined extracts were washed with saturated aqueous $NaHCO_3$, saturated aqueous NaCl, dried ($MgSO_4$), filtered and evaporated to yield 70.0 g white solid, M+166.

EXAMPLE 100

1-Tosyloxy-3-(3-methoxyphenyl)-propane

A solution of 3-(3-methoxyphenyl)-propanol (69 g, 0.42 mole) and pyridine (400 mL) was stirred at 5° C. as p-toluenesulfonyl chloride (87 g, 0.46 mole) was added portionwise. The reaction mixture was stirred at room temperature for 2 hours, then was poured onto ice/concentrated HCl and was extracted with ether. The extracts were washed with 2N HCl, wawter, saturated aqueous NaCl, dried ($MgSO_4$), filtered, and evaporated to yield 126 g yellow oil, (95%); M+320.

EXAMPLE 101

1-Cyano-3-(3-methoxyphenyl)-propane

A solution of 1-tosyloxy-3-(3-methoxyphenyl)propane (125 g, 0.39 mole) and DMF (400 mL) was stirred at 0° as a solution of KCN (30 g, 0.46 mole) and water (70 mL) was added dropwise. The reaction mixture was stirred at 65°–70° for 1 hour, was cooled to room temperature and poured onto ice water. The solution was extracted with ether. The extracts were washed with water, saturated aqueous NaCl, dried ($MgSO_4$), filtered, and evaporated to yield 62 g yellow oil, (91%), M+175.

EXAMPLE 102

γ-(3-methoxyphenyl)-butyric acid

A solution of 1-cyano-3-(3-methoxyphenyl)-propane (61.1 g, 0.35 mole), KOH (150 g), and ethanol (500 mL) was stirred at reflux for 6 hours. After cooling to 0° the reaction mixture was acidified with concentrated HCl and was extracted with $CH_2Cl_2$. The extracts were washed with water, saturated aqueous NaCl, dried ($MgSO_4$), filtered, and evaporated to yield 53.3 g white solid, (78.5%); M+194.

EXAMPLE 103

5-Bromo-8-methoxy-α-tetralone

A solution of γ-(3-methoxyphenyl)-butyric acid (32 g, 0.165 mole) and $CH_2Cl_2$ (650 mL) was stirred at 0° as a solution of bromine (9 mL, 28.8 g, 0.18 mole) and $CH_2CL_2$ (100 mL) was added dropwise. The reaction mixture was stirred for 1 hour at 0°, then was washed with water, saturated aqueous NaCl, dried ($MgSO_4$), filtered, and ether added. The solid was filtered, dried (in-vacuo) to yield 29 g white solid, (65%); M+272; mp 93°–5° C.

EXAMPLE 103a

5-Bromo-8-methoxy-α-tetralone

A mixture of 4-(2-bromo-5-methoxyphenyl)-butyric acid (28 g, 0.10 mole) and polyphosphoric acid (450 g) was heated at 100° C. for 0.5 hour. The reaction mixture was poured onto ice water and was extracted with $CH_2Cl_2$. The extracts were washed with water, saturated aqueous $NaHCO_3$, saturated aqueous NaCl, dried (MgSO$_4$), filtered, and evaporated (in-vacuo) to yield 25.5 g yellow oil, (97%); M+254.

EXAMPLE 104

5-Bromo-1-cyano-3,4-dihydro-8-methoxy naphthalene

A solution of 5-bromo-8-methoxy-α-tetralone (10.0 g, 39.2 mmole), trimethylsilycyanide (6.3 mL, 47.1 mmole), catalytic AlCl$_3$, and benzene (5 mL) was stirred under N$_2$ at 70° for 2 hours. After cooling to room temperature, toluene (125 mL) was added, followed by p-toluenesulfonic acid (5 g). The reaction mixture was stirred at reflux for 1.5 hours, was cooled to room temperature and toluene was removed (in-vacuo). Water was added and the solution was extracted with CH$_2$Cl$_2$. The extracts were washed with H$_2$O, saturated aqueous NaHCO$_3$, saturated aqueous NaCl, dried (MgSO$_4$), filtered and evaporated to yield 9.96 g yellow solid, (96%).

EXAMPLE 105

5-Bromo-1,2-dicyano-8-methoxy tetralin

Using the procedure as described in example 2, but starting with 5-bromo-1-cyano-3,4-dihydro-8-methoxynaphthalene, afforded the desired compound, (45%).

EXAMPLE 106

6-Bromo-3a,4,5,9b-tetrahydro-9-methoxy-1H-benz[e]isoindole-1,3-(2H)-dione

Using the procedure of example 3, but starting with the product of example 105 afforded the desired compound; M+309; mp 191°-3° C.

EXAMPLE 107

6-Bromo-2,3,3a,4,5,9b-hexahydro-9-methoxy-1H-benz[e]isoindole hydrochloride

Using the procedure of example 5, but starting with the product from example 106, the desired compound was obtained; M+281; mp 184°-5° C.

EXAMPLE 108

6-Bromo-3a,4,5,9b-tetrahydro-9-methoxy-2-methyl-1H-benz[e]isoindole-1,3-(2H)-dione Using the procedure as described in example 64, but starting with 6-bromo-3a,4,5,9b-tetrahydro-9-methoxy-1H-benz[e]isoindole-1,3-(2H)-dione afforded the desired compound; M+323; mp 201°-2° C.

EXAMPLE 109

6-Bromo-2,3,3a,4,5,9b-hexahydro-9-methoxy-2-methyl-1H-benz[e]isoindole hydrochloride Using the procedure of example 5, but starting with the product from example 108, the desired compound was obtained; M+295; mp 227°-8° C.

EXAMPLE 110

6-Bromo-2,3,3a,4,5,9b-hexahydro-9-hydroxy-1H-benz[e]isoindole hydrobromide

Using the procedure of example 7, but starting with 6-bromo-2,3,3a,4,5,9b-hexahydro-9-methoxy-1H-benz[e]isoindole hydrochloride afforded the desired compound; M+267; mp 240°-2° C.

EXAMPLE 111

6-Bromo-2-ethyl-3a,4,5,9b-tetrahydro-9-methoxy-1H-benz[e]isoindole-1,3-(2H)-dione Using the procedure of example 64, but starting with 6-bromo-3a,4,5,9b-tetrahydro-9-methoxy-1H-benz[e]isoindole-1,3-(2H)-dione and ethyl iodide instead of methyl iodide afforded the desired compound; M+337; mp 170°-4°.

EXAMPLE 112

6-Bromo-2-ethyl-3a,4,5,9b-tetrahydro-9-methoxy-1H-benz[e]isoindole-1,3-(2H)-dione Using the procedure of example 5, but starting with 6-bromo-2-ethyl-3a,4,5,9b-tetrahydro-9-methoxy-1H-benz[e]isoindole-1,3-(2H)-dione afforded the desired compound; M+309; mp 184°-5° C.

EXAMPLE 113

1-Cyano-3,4-dihydro-5,8-dimethoxynaphthalene

A solution of 5,8-dimethoxy-α-tetralone (106 g, 49.4 mmole), trimethylsilylcyanide (11.2 mL, 84 mmole), and catalytic AlCl$_3$ was stirred overnight at 85°-90°. After cooling to room temperature, pyridine (80 mL) and POCl$_3$ (142 mL, 1.48 mole) were added. The reaction mixture was stirred at reflux for 4 hours. After cooling to room temperature, the reaction mixture was poured onto ice/6N HCl. The solution was extracted with ether. The extracts were washed with 1N HCl, 1N KOH, water, saturated aqueous NaCl, dried (MgSO$_4$), filtered, and evaporated (in-vacuo) to yield 8.0 g tan solid (75%); M+215.

EXAMPLE 114

1,2-Dicyano-5,8-dimethoxytetralin

Using the procedure as described in example 2, but starting with 1-cyano-3,4-dihydro-5,8-dimethoxynaphthalene affording the desired compound; mp 126°-7° C.

EXAMPLE 115

3a,4,5,9b-Tetrahdyro-6,9-dimethoxy-1H-benz[e]isoindole-1,3-(2H)-dione

Using the procedure described in example 3, but starting with 1,2-dicyano-5,8-dimethoxytetralin afforded the desired compound; M+261; mp 135°-6° C.

EXAMPLE 116

2,3,3a,4,5,9b-Hexahydro-6,9-dimethoxy-1H-benz[e]isoindole hydrochloride

Using the procedure of example 5, and the product from example 115, the desired compound was obtained; M+233; mp 165°-8° C.

EXAMPLE 117

3a,4,5,9b-Tetrahydro-6,9-dimethoxy-2-methyl-1H-benz[e]isoindole-1,3-(2H)-dione

Using the procedure of example 64, and the product from example 115, the desired product was obtained, M+225; mp 213°-15° C.

EXAMPLE 118

2,3,3a,4,5,9b-Hexahydro-6,9-dimethoxy-2-methyl-1H-benz[e]isoindole hydrochloride Using the procedure of example 5, and the product from example 117, the desired product was obtained; M+247; mp 160°-4° C.

EXAMPLE 119

2-Ethyl-3a,4,5,9b-tetrahydro-6,9-dimethoxy-1H-benz[e]isoindole-1,3-(2H)-dione

Using the procedure of example 64, and the product from example 115, and ethyl iodide in place of methyl iodide, the desired compound was obtained; M+289; mp 115°-16° C.

EXAMPLE 120

2-Ethyl-2,3,3a,4,5,9b-hexahydro-6,9-dimethoxy-1H-benz[e]isoindole hydrochloride

Using the procedure of example 5 with 2-ethyl-3a,4,5,9b-tetrahydro-6,9-dimethoxy-1H-benz[e]isoindole-1,3-(2H)-dione afforded the product; M+261; mp 148°-51° C.

EXAMPLE 121

3a,4,5,9b-Tetrahydro-6,9-dimethoxy-2-propyl-1H-benz[e]isoindole-1,3-(2H)-dione

Using the procedure of example 64 and the product from example 115 with propylbromide afforded the compound; M+303; mp 112°-13° C.

EXAMPLE 122

2,3,3a,4,5,9b-Hexahydro-6,9-dimethoxy-2-propyl-1H-benz[e]isoindole hydrochloride Using the procedure of example 5 with 3a,4,5,9b-tetrahydro-6,9-dimethoxy-2-propyl-1H-benz[e]isoindole-1,3-(2H)-dione, afforded the product; M+275; mp 85°-8° C.

EXAMPLE 123

2,3,3a,4,5,9b-Hexahydro-9-methoxy-2-methyl-6-thiomethyl-1H-benz[e]isoindole hydrochloride Dry distilled THF (3.9 mL) was stirred under $N_2$ at $-78°$ C. as n-butyllithium (3.2 mL, 8.34 mmole, 2.6M in hexane) was added. After adding dropwise a suspension of 6-bromo-2,3,3a,4,5,9b-hexahydro-9-methoxy-2-methyl-1H-benz[e]isoindole free base (0.72 g, 2.45 mmole) in THF (4.9 mL) the reaction mixture was stirred at $-78°$ C. for 35 minutes, then a solution of dimethyldisulfide (0.98 mL, 11.1 mmole) and THF (15.7 mL) was added dropwise. The reaction mixture was stirred for 5 hours at $-78°$, then was allowed to warm to room temperature overnight. The reaction mixture was quenched with 10% aqueous HCl. The solvents were removed in-vacuo and water was added to the residue. The neutral ether extracts were set aside and the aqueous layer was basified with 1N KOH and was extracted with $CH_2Cl_2$. The combined $CH_2Cl_2$ layers were washed with water, saturated aqueous NaCl, dried (MgSO$_4$), filtered, evaporated, converted to the HCl salt and crystallized from ethanol/ether to yield 0.310 g white solid; mp 168°-70°; M+263.

EXAMPLE 124

2,3,3a,4,5,9-Hexahydro-7-methoxy-2-methyl-6-thiomethyl-1H-benz[e]isoindole hydrochloride Using the procedure of example 123, with 6-bromo-2,3,3a,4,5,9b-hexahydro-7-methoxy-2-methyl-1H-benz[e]isoindole free base, afforded the product, mp 144°-6° C.; M+263.

EXAMPLE 125

5-Methoxy-8-hydroxy-α-tetralone

A mixture of 5,8-dimethoxy-α-tetralone (10 g, 48.5 mmole), glacial acetic acid (110 mL), and concentrated HCl (460 mL) was stirred at reflux for 3 hours. After cooling to room temperature, the reaction mixture was poured onto ice and the solid was filtered, washed with water, and dried (in-vacuo) to yield 6.3 g red powder; M+192.

EXAMPLE 126

5-Methoxy-8-phenethoxy-α-tetralone

A mixture of 8-hydroxy-5-methoxy-α-tetralone (6.3 g, 32.8 mmole), $K_2CO_3$ (36 g), 2-bromoethylbenzene (16.4 mL, 0.12 mole), 2-butanone (220 mL), and 18-crown-6 (catalytic) was stirred at reflux for 72 hours. After cooling to room temperature the reaction mixture was filtered, and evaporated (in-vacuo). The residue was dissolved in $CH_2CL_2$, washed with 1N HCl, water, saturated aqueous NaCl, dried (MgSO$_4$), filtered and evaporated to yield 13.5 g orange oil which was purified by column chromatography (silica gel) to yield 4.9 g white solid, M+296.

EXAMPLE 127

1-Cyano-3,4-dihydro-5-methoxy-8-phenethoxynaphthalene

Using the procedure of example 112, with the product from example 126 afforded the compound; M+305.

EXAMPLE 128

1,2-Dicyano-5-methoxy-8-phenethoxytetralin

Using the procedure of example 2 with the product from example 127 afforded the compound; M+247.

EXAMPLE 129

3a,4,5,9b-Tetrahydro-6-methoxy-9-phenethoxy-1H-benz[e]isoindole-1,3-(2H)-dione

Using the procedure of example 3 with the product from example 128 afforded the compound; M+351.

EXAMPLE 130

2-Ethyl-3a,4,5,9b-tetrahydro-6-methoxy-9-phenethoxy-1H-benz[e]isoindole-1,3-(2H)-dione Using the procedure of example 64 with the product of example 129 and ethyl iodide in place of methyl iodide gave the compound; M+379.

EXAMPLE 131

2-Ethyl-2,3,3a,4,5,9b-hexahydro-6-methoxy-9-phenethoxy-1H-benz[e]isoindole hydrochloride Using the procedure of example 5 with the product of example 130 gave the compound; mp 171°-2° C.; M+351.

EXAMPLE 132

5-Methoxy-8-(3-phenylpropyloxy)-α-tetralone

Using the procedure of example 126 with 1-bromo-3-phenylpropane gave the compound; M+310.

EXAMPLE 133

1-Cyano-3,4-dihydro-5-methoxy-8-(3-phenylpropyloxy)naphthalene

Using the procedure of example 113 with the product from example 132 gave the compound; M+319.

EXAMPLE 134

1,2-Dicyano-5-methoxy-8-(3-phenylpropyloxy)-tetralin

Using the procedure of example 2 with the product of example 133 gave the compound; M+346.

EXAMPLE 135

3a,4,5,9b-Tetrahydro-6-methoxy-9-(3-phenylpropyloxy)-1H-benz[e]isoindole-1,3-(2H)-dione Using the product of example 3 with the product from example 134 gave the compound; M+365.

EXAMPLE 136

2-Ethyl-3a,4,5,9b-tetrahydro-6-methoxy-9-(3-phenylpropyloxy)-1H-benz[e]isoindole-1,3-(2H)-dione Using the procedure of example 64 with the product of example 135 and ethyl iodide gave the compound; M+393.

EXAMPLE 137

2-Ethyl-2,3,3a,4,5,9b-hexahydro-6-methoxy-9-(3-phenylpropyloxy)-1H-benz[e]isoindole hydrochloride Using the procedure of example 5 with the product from example 136 gave the compound; mp 70°-3° C.; M+365.

EXAMPLE 138

5-Methoxy-8-[3-(4-methylphenyl)propyloxy]-α-tetralone

Using the procedure of example 126 with 1-bromo-3-(4-methylphenyl)propane gave the compound; M+324.

EXAMPLE 139

1-Cyano-3,4-dihydro-8-[3-(4-methylphenyl)-propyloxy]naphthalene

Using the procedure of example 113 with the product from example 138 gave the compound; M+333.

EXAMPLE 140

1,2-Dicyano-5-methoxy-8-[3-(4-methylphenyl)-propyloxy]tetralin

Using the procedure of example 2 with the product from example 139 gave the compound; M+360.

EXAMPLE 141

3a,4,5,9b-Tetrahydro-6-methoxy-9-[3-(4-methylphenyl)propyloxy]-1H-benz[e]isoindole-1,3-(2H)-dione Using the procedure of example 3 with the product from example 140 gave the compound; M+379.

EXAMPLE 142

2-Ethyl-3a,4,5,9b-tetrahydro-6-methoxy-9-[3-(4-methylphenyl)-propyloxy]-1H-benz[e]isoindole-1,3-(2H)-dione Using the procedure of example 64 with the product from example 141 gave the compound; M+407.

EXAMPLE 143

2-Ethyl-2,3,3a,4,5,9b-hexahydro-6-methoxy-9-[3-(4-methylphenyl)-propyloxy]-1H-benz[e]isoindole hydrochloride Using the procedure of example 5 with the product from example 142 gave the compound; mp 136°-40° C.; M+379.

EXAMPLE 144

8-[3-(4-Fluorophenyl)-propyloxy]-5-methoxy-α-tetralone

Using the procedure of example 126 with 1-chloro-3-(4-fluorophenyl)-propane gave the compound; M+328.

EXAMPLE 145

1-Cyano-8-[3-(4-fluorophenyl)propyloxy]-3,4-dihydro-5-methoxynaphthalene

Using the procedure of example 113 with the product from example 144 gave the compound; M+337.

EXAMPLE 146

1,2-Dicyano-8-[3-(4-fluorophenyl)-propyloxy]-5-methoxytetralin

Using the procedure of example 2 with the product from example 145 gave the compound; M+364.

EXAMPLE 147

9-[3-(4-Fluorophenyl)-propyloxy]-3a,4,5,9b-tetrahydro-6-methoxy-1H-benz[e]isoindole-1,3-(2H)-dione Using the procedure of example 3 with the product from example 146 gave the compound; M+383; mp 137°-9° C.

EXAMPLE 148

2-Ethyl-9-[3-(4-fluorophenyl)-propyloxy]-3a,4,5,9b-tetrahydro-6-methoxy-1H-benz[e]isoindole-1,3-(2H)-dione Using the procedure of example 64 with the product from example 147 and ethyl iodide gave the compound; M+411.

EXAMPLE 149

2-Ethyl-9-[3-(4-fluorophenyl)-propyloxy]-2,3,3a,4,5,9b-hexahydro-6-methoxy-1H-benz[e]isoindole hydrochloride Using the procedure of example 5 with the product from example 148 gave the compound; M+383; mp 90°-2° C.

EXAMPLE 150

5-Methoxy-8-(4-phenylbutyloxy)-α-tetralone

Using the procedure from example 126 and 1-bromo-4-phenylbutane afforded the desired product.

EXAMPLE 151

2-Ethyl-2,3,3a,4,5,9b-hexahydro-6-methoxy-9-(4-phenylbutyloxy)-1H-benz[e]isoindole hydrochloride Using the procedures from examples 127–131 with the product from example 150 afforded the desired product.

EXAMPLE 152

5-Methoxy-8-[3-(3-nitrophenyl)-propyloxy]-α-tetralone

Using the procedure of example 126 with 1-bromo-3-(3-nitrophenyl)-propane afforded the desired compound.

EXAMPLE 153

2-Ethyl-2,3,3a,4,5,9b-hexahydro-6-methoxy-9-[3-(3-nitrophenyl)propyloxy]-1H-benz[e]isoindole hydrochloride Using the procedures of examples 127–131 and the product from example 152 afforded the desired compound.

EXAMPLE 154

9-[3-(3-Aminophenyl)-propyloxy]-2-ethyl-2,3,3a,4,5,9b-hexahydro-6-methoxy-1H-benz[e]isoindole dihydrochloride The product from example 153 was catalytically reduced at 3 atmospheres pressure of hydrogen in the presence of Raney Nickel, and 2-methoxyethanol. The reaction was filtered and the solvent evaporated to dryness followed by crystallization from EtOH/Et$_2$O.

EXAMPLE 155

5-Methoxy-8-(2-phenethyl)-α-tetralone

A solution of 4-[(2-methoxy-5-phenethyl)-phenyl]-butyric acid (14.5 g, 50 mmole) and CHCl$_3$ (150 mL) was stirred at room temperature as a solution of thionyl chloride (11.0 mL, 150 mmole) and DMF (0.1 mL) was added. The reaction mixture was stirred at reflux for 2 hours. Solvents were removed (in-vacuo). The acid chloride was stirred at 0° with CH$_2$Cl$_2$ (250 mL) as AlCl$_3$ (33 g, 250 mmole) was added. After stirring at room temperature for 18 hours the reaction mixture was poured onto ice, extracted with CH$_2$Cl$_2$, washed with water, dried, filtered, evaporated and chromatographed to yield 8.9 g. (64%).

EXAMPLE 156

1-Cyano-3,4-dihydro-5-methoxy-8-(2-phenethyl)-naphthalene

Using the procedure of example 114, but starting with 5-methoxy-8-(2-phenethyl)-α-tetralone afforded the desired compound. (86%).

EXAMPLE 157

1,2-Dicyano-5-methoxy-8-(2-phenethyl)-α-tetralone

Using the procedure of example 2, but starting with the product from example 156, the desired compound was obtained.

EXAMPLE 158

3a,4,5,9b-Tetrahydro-6-methoxy-9-(2-phenethyl)-1H-benz[e]isoindole-1,3-(2H)-dione Using the procedure of example 3, but starting with the product of example 157, afforded the desired compound.

EXAMPLE 159

2-Ethyl-3a,4,5,9b-tetrahydro-6-methoxy-9-(2-phenethyl)-1H-benz[e]isoindole-1,3-(2H)-dione Using the procedure of example 64 with the product from example 158 gave the desired product.

EXAMPLE 160

2-Ethyl-2,3,3a,4,5,9b-hexahydro-6-methoxy-9-(2-phenethyl)-1H-benz[e]isoindole oxalate Using the procedure of example 3 with the product from example 159 and oxalic acid instead of HCl gave the compound; mp 179°–80° C.

EXAMPLE 161

2-Ethyl-2,3,3a,4,5,9b-hexahydro-6-methoxy-9-(4-phenbutyl)-1H-benz[e]isoindole hydrochloride Using the procedures of examples 156–160 with 5-methoxy-8-(4-phenbutyl)-α-tetralone gave the desired product.

The therapeutic activity of the compounds can be demonstrated in vivo by their ability to decrease arterial blood pressure and/or heart rate in the spontaneously hypertensive rat as follows. A group of Okamoto rats, which develop hypertension spontaneously when reaching young adulthood, are deprived of food for a period of 16 hours and are placed in semi-restraining wire mesh cylinders maintained at a constant temperature of 36° C. An occluding cuff, operatively connected to a programmed sphygmomanometer, is placed over the tail of each rat of the group and retained near the tail base. The pressure of each cuff is automatically, cyclically increased within the range of from 0 to 250 mm Hg. at the rate of 10 mm Hg./sec., the total inflation and deflation time of each cycle being 50 seconds, with a 10 second rest period between cycles. A photocell is placed distal to the cuff to detect pulses resulting from the forward motion of blood flow with each heartbeat of the rat. As the pressure in the cuff increases, measurable pulses disappear at the point where the cuff pressure equals the arterial blood pressure. Measurable pulses reappear during deflation at approximately the same pressure, and arterial blood pressure is thereby established by cuff pressure at the point of pulse appearance. The heart rate is determined from the arterial pulse wave. A 100 mg./kg. dose of a test compound of formula I is administered orally to each rat of the test group, and five interference-free signals are recorded on a Model 7 Grass polygraph for each rat at various measurement periods following administration. By following the foregoing procedure, the tested preferred compounds of the invention are shown to decrease the arterial blood pressure and/or heart rate of rats of the group.

In addition to the antihypertensive use of the compounds of the invention, the compounds have been found to be effective sedatives.

The compounds of the invention can be administered in any effective pharmaceutically acceptable form to warm blooded animals, e.g., in oral, parenteral or infusable dosage forms, or as a buccal or nasal spray. Suitable parenteral routes of administration include, for example, intramuscular, iontophoretic, intravenous, intraperitoneal or subcutaneous administration of the compounds.

In addition to the active compounds, compositions according to this invention for parenteral injection may comprise pharmaceutically acceptable sterile aqueous or nonaqueous solutions, suspensions or emulsions. Examples of suitable nonaqueous carriers, diluents, solvents or vehicles include propylene glycol, polyethylene glycol, vegetable oils, such as olive oil, and injectable organic esters such as ethyl oleate. Such compositions may also contain adjuvants such as preserving, wetting, emulsifying, and dispersing agents. They may be sterilized, for example, by filtration through a bacteria-retaining filter, or by incorporating sterilizing agents into the compositions. They can also be manufactured in the form of sterile solid compositions which can be dissolved in sterile water, or other sterile injectable medium, immediately before use.

Solid dosage forms for oral administration include capsules, tablets, pills, powders and granules. In such solid dosage forms, the active compound may be admixed with at least one inert diluent such as sucrose, lactose or starch. Such dosage forms may also comprise, as is normal practice, additional substances other than inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups and elixirs containing inert diluents commonly used in the art, such as water. Besides such inert diluents, compositions may also comprise adjuvants, such as wetting agents, emulsifying and suspending agents, and sweetening, flavoring and perfuming agents.

Actual dosage levels of active ingredient in the compositions of the invention may be varied so as to obtain an amount of active ingredient effective to obtain a desired therapeutic response for a particular composition and method of administration. The selected dosage level therefore depends upon the desired therapeutic effect, on the route of administration, on the desired duration of treatment and other factors. Generally, dosage levels of about 0.1 to about 200, more preferably about 0.5 to about 150 and most preferably about 1 to about 125 mg. of active ingredient per kg. of body weight per day are administered orally to a mammalian patient suffering from hypertension. If desired, the daily dose may be divided into multiple doses for administration, e.g., two to four separate doses per day.

What is claimed is:

1. A compound of the formula

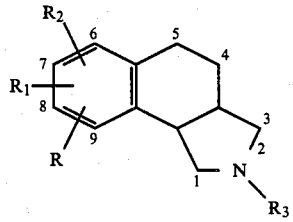

wherein R, $R_1$ and $R_2$ are independently selected from hydrogen, loweralkyl of 1 to 4 carbon atoms, hydroxy, loweralkoxy of 1 to 3 carbon atoms, allyloxy, benzyloxy, benzoyloxy, thiomethyl, halo, or

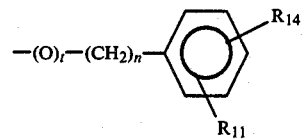

wherein t is 0 or 1, n is 0 to 5, and $R_{11}$ and $R_{14}$ are independently selected from hydrogen, halo, hydroxy, loweralkyl of 1 to 4 carbon atoms, loweralkoxy of 1 to 3 carbon atoms or amino; or R and $R_1$, or $R_1$ and $R_2$ can be taken together to form a methylenedioxy or ethylenedioxy bridge; with the proviso that at least one of R, $R_1$ or $R_2$ must be other than hydrogen and the proviso that two of R, $R_1$ or $R_2$ must be other than methoxy in the 7 and 8 positions when the remaining one of R, $R_1$ or $R_2$ is hydrogen; and $R_3$ is hydrogen, loweralkyl of 1 to 4 carbon atoms, halo-substituted loweralkyl of 1 to 4 carbon atoms, amino-substituted loweralkyl of 1 to 4 carbon atoms, amino-substituted arylalkyl, allyl, thioloweralkyl, loweralkanol, or

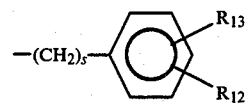

wherein $R_{12}$ and $R_{13}$ are independently selected from hydrogen, hydroxy, amino, loweralkoxy of 1 to 3 carbon atoms and s is 1 to 3; or

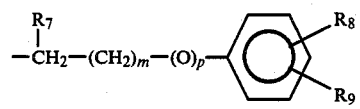

wherein m is 0, 1 or 2, p is 0 or 1, $R_7$ is hydrogen or loweralkyl of 1 to 4 carbon atoms and $R_8$ and $R_9$ are independently selected from hydrogen, hydroxy, methoxy, loweralkyl of 1 to 4 carbon atoms, or halo, or $R_8$ and $R_9$ can be taken together to form a methylenedioxy or ethylenedioxy bridge; or 1,4-benzodioxan of the formula

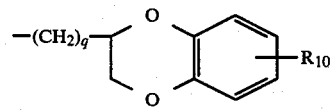

wherein q is 1, 2 or 3, and $R_{10}$ is hydrogen, methoxy, amino, or halo; and the pharmaceutically acceptable salts thereof.

2. A compound of claim 1 wherein one of R, $R_1$, and $R_2$ is hydrogen.

3. A compound of claim 2 wherein the remaining two of R, $R_1$ and $R_2$ are hydroxy.

4. A compound of claim 2 wherein the remaining two of R, $R_1$ and $R_2$ are thiomethyl and methoxy.

5. A compound of claim 2 wherein the remaining two of R, $R_1$ and $R_2$ are halo and methoxy.

6. A compound of claim 2 wherein the remaining two of R, $R_1$ and $R_2$ are methoxy and

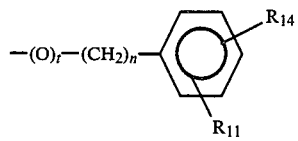

wherein t, n, $R_{11}$ and $R_{14}$ are as defined in claim 1.

7. A compound of claim 1 wherein two of R, $R_1$ and $R_2$ are hydrogen and the remaining one of R, $R_1$ and $R_2$ is methoxy.

8. A compound of claim 1 wherein two of R, $R_1$ and $R_2$ are hydroxy and the remaining one of R, $R_1$ and $R_2$ is loweralkyl of 1 to 4 carbon atoms.

9. A compound of claim 1 wherein two of R, $R_1$ and $R_2$ are hydroxy and the remaining one of R, $R_1$ and $R_2$ is arylalkyl.

10. A compound of claim 1 wherein two of R, $R_1$ and $R_2$ are hydroxy and the remaining one of R, $R_1$ and $R_2$ is

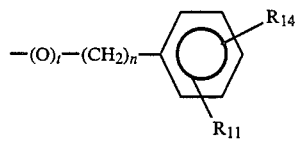

wherein t, n, $R_{11}$ and $R_{14}$ are as defined in claim 1.

11. A compound of claims 1 or 3 wherein $R_3$ is hydrogen.

12. A compound of claims 1, 2, 3, 4, 5, 6, 7, 8, 9, or 10 wherein $R_3$ is loweralkyl.

13. A compound of claims 1 or 3 wherein $R_3$ is allyl.

14. A compound of claim 1 wherein $R_3$ is aryloxyalkyl of the formula

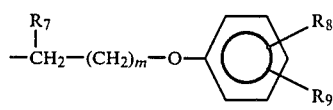

wherein m, $R_7$, $R_8$ and $R_9$ are as defined in claim 1.

15. A compound of claim 1 wherein $R_3$ is arylalkyl of the formula

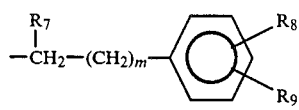

wherein m, $R_7$, $R_8$ and $R_9$ are as defined in claim 1.

16. A compound of claims 1 or 7 wherein $R_3$ is a benzodioxane of the formula

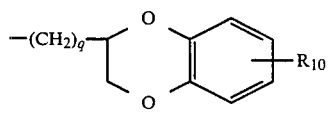

wherein q and $R_{10}$ are as defined in claim 1.

17. A pharmaceutical composition for sedation or treating hypertension comprising a pharmaceutical carrier and sedative or antihypertensive effective amount of the compound of claim 1.

* * * * *